US006274369B1

(12) United States Patent
Donahue, Jr. et al.

(10) Patent No.: US 6,274,369 B1
(45) Date of Patent: Aug. 14, 2001

(54) METHOD CAPABLE OF INCREASING COMPETENCY OF BACTERIAL CELL TRANSFORMATION

(75) Inventors: Robert A. Donahue, Jr., Falls Church, VA (US); Robert L. Bebee, Gaithersburg, MD (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 08/790,820

(22) Filed: Jan. 30, 1997

Related U.S. Application Data

(60) Provisional application No. 60/011,040, filed on Feb. 2, 1996.

(51) Int. Cl.$^7$ .............................. C12N 1/20; C12N 15/74
(52) U.S. Cl. .................. 435/252.33; 435/476; 435/488
(58) Field of Search ................ 435/252.3, 252.33, 435/172–3, 440, 476, 488

(56) References Cited

U.S. PATENT DOCUMENTS

| | | | |
|---|---|---|---|
| 3,843,453 | 10/1974 | Freake | 195/103.5 |
| 4,038,143 | 7/1977 | Juni | 195/100 |
| 4,446,230 | 5/1984 | Zubrzycki | 435/6 |
| 4,520,019 | 5/1985 | Ribi et al. | 424/195.1 |
| 4,681,852 | 7/1987 | Tribe | 435/108 |
| 4,808,404 | 2/1989 | Bhogal | 424/88 |
| 4,824,938 | 4/1989 | Koyama et al. | 530/351 |
| 4,851,348 | 7/1989 | Hanahan | 435/252.33 |
| 4,891,319 | 1/1990 | Roser et al. | 435/188 |
| 4,950,609 | 8/1990 | Tischer et al. | 435/18 |
| 4,981,797 | 1/1991 | Jesse et al. | 435/172.3 |
| 5,045,446 | 9/1991 | Goodrich, Jr. et al. | 435/2 |
| 5,059,518 | 10/1991 | Kortright et al. | 435/6 |
| 5,098,893 | 3/1992 | Franks et al. | 514/54 |
| 5,292,507 | 3/1994 | Charley | 424/93 |
| 5,425,951 | 6/1995 | Goodrich, Jr. et al. | 424/520 |
| 5,512,468 * | 4/1996 | Greener | 435/172.3 |
| 5,891,692 | 4/1999 | Bloom et al. | 435/172.3 |

FOREIGN PATENT DOCUMENTS

| | | |
|---|---|---|
| A-27434/88 | 6/1989 | (AU) . |
| 0 383 569 A2 | 8/1990 | (EP) . |
| 0 508 496 A1 | 10/1992 | (EP) . |
| WO 98/49266 | 11/1998 | (WO) . |

OTHER PUBLICATIONS

Liss, Laura R. New M13 Host: DH5αF' Competent Cells. Focus vol. 9, No. 3, 1987.

E. Neumann et al., Gene Transfer Into Mouse Lyoma Cells by Electroporation in High Electric Fields, The EMBO Journal, vol. 1, No. 7, pp. 841–845 (1982).

Herbert W. Boyer et al., An Improved Method for Transformation of *Escherichia coli* with ColE1 Derived Plasmids, Genetic Engineering, Proceedings of the International Symposium on Genetic Engineering: Scientific Developments and Practical Applications held in Milan, Italy, Genetic Engineering, pp. 17–23 (1978).

Akira Taketo, Sensitivity of *Escherichia coli* to Viral Nuclei Acid, The Journal of Biochemistry, V. 75, No. 4. pp. 895–904 (1974).

A.G. Walton, M1 3mp2 and Derivatives: A Molecular Cloning System for DNA Sequencing, Strand–Specific Hybridization, and In Vitro Mutagenesis, Recombinant DNA, Proceedings of the Third Cleveland Symposium on Macromolecules, Cleveland, Ohio, pp. 143–153 (1981).

J. Sambrook et al., *Molecular Cloning*, p. 1.14 (1989).

Alex Levinson et al., Minimal Size Plasmids Containing an M13 Origin for Production of Single–Strand Transducing Particles, Journal of Molecular and Applied Genetics, pp. 507–517 (1984).

Newman et al., Cloning and Expression of the ilvB Gene of *Escherichia coli* K–12, Molecular & General Genetics, V. 186, pp. 378–384, (1982).

M. Mandel et al., Calcium–Dependent Bacteriophage DNA Infection, Journal of Molecular Biology, V. 53, No. 1, 14, pp. 159–162 (1970).

J. L. Hamrick et al., Microgeographical Variation in Allozyme Frequencies in Avena Barbata, Proceedings of the National Academy of Sciences of the U.S.A., vol. 69, No. 8, pp. 2100–2104 (1972).

Akira Taketo, Sensitivity of *Escherichia coli* to Viral Nucleic Acid, X , Zeitschrift Fur Naturforschung V. 30c, pp. 520–522, (1975).

Akira Taketo, Sensitivity of *Escherichia coli* to Viral Nucleic Acid, XII, Zeitschrift Fur Naturforschung V. 32c, pp. 429–433, (1977).

Luciana Dente et al., pEMBL: A New Family of Single Stranded Plasmids, Nucleic Acids Research, V. 11, No. 6, pp. 1645–1655 (1983).

Huntington Potter, Electroporation in Biology: Methods, Applications, and Instrumentation, Analytical Biochemistry, V. 174, No. 2, pp. 361–373 (1988).

U. Zimmerman et al., Electric Field–Induced Cell–to–Cell Fusion, The Journal of Membrane Biology, V. 67, No. 3 pp. pp. 165–182 (1982).

(List continued on next page.)

*Primary Examiner*—Nashaat T. Nashed
(74) *Attorney, Agent, or Firm*—Sterne, Kessler, Goldstein & Fox P.L.L.C.

(57) ABSTRACT

The invention concerns bacterial strains capable of enhanced transformation efficiencies that are produced by the introduction of the F' genetic material. The invention also concerns processes for producing transformable competent bacteria with enhanced transformation efficiencies.

14 Claims, No Drawings

OTHER PUBLICATIONS

Dower et al., High Efficiency Transformation of E.Coli by High Voltage Electroporation, V. 16, No. 13, pp. 6127–6245 (1988).

Dagert et al., Prolonged Incubation in Calcium Chloride Improves the Competence of *Escherichia coli* Cells, Gene, V. 6, No. 1, pp. 23–28 (1979).

Meselson et al., DNA Restriction Enzyme from E. Coli, Nature, V. 217, pp. 1110–1114 (1968).

Zagursky et al., Cloning Vectors that Yield High Levels of Single–Stranded DNA For Rapid Sequencing, Gene, V. 27, pp. 183–191 (1984).

Vieira et al., Production of Single–Stranded Plasmid DNA, Methods in Enzymology, V. 153, pp. 3–11 (1987).

Bullock et al., XL1–Blue: A High Efficiency Plasmid Transforming recA *Escherichia coli* Strain With Beta–Galactosidase Selection, Biotechniques, V. 5, No. 4, pp. 376–378 (1987).

Celese Yanisch–Perron et al., Improved M13 Phage Cloning Vectors and Host Strains: Nucleotide Sequences of the M13mp18 and pUC19 Vectors, vol. 33, Gene, pp. 103–119 (1985).

Douglas Hanahan, Studies on Transformation of *Escherichia coli* with Plasmids, Journal of Molecular Biology, V. 166, No. 4, pp. 557–580 (1983).

Tucker et al., Structural and Functional Analysis of the par Region of the pSC 101 Plasmid, Cell, V. 38, No. 1, pp. 191–201 (1984).

Lui et al., Comparison of Various Competent Cell Preparation Methods for High Efficiency DNA Transformation, BioTechniques, V. 8, No. 1, pp. 21–25 (1990).

Old & Primrose, Principles of Gene Manipulation: An Introduction to Genetic Engineering, Blackwell, Science pp. 6–21 (1995).

Hanahan et al., In *Escherichia coli* and Salmonella, Mechanisms of DNA Transformation, Cellular and Molecular Biology, 2nd Ed. pp. 2448–2459 (1996) ASM PRESS.

GIBCO–BRL Catalog, Life Technologies, 1993–1994, pp. 9–6 and 9–10.*

Anderson, D.M.W. and I.C.M. Dea, "Recent advances in the chemistry of Acacia gums," *J. Soc. Cosmet. Chem.* 22: 61–76 (1971).

Alexander, D.C. et al., "A simplified and efficient vector–primer cDNA cloning system," *Gene* 31:79–89 (1984).

Chung, C.T. et al., "One–step preparation of competent *Escherichia coli*: Transformation and storage of bacterial cells in the same solution," *Proc. Natl. Acad. Sci. USA* 86:2172–2175 (1989).

Cohen, S.N. et al., "Nonchromosomal Antibiotic Resistance in Bacteria: Genetic Transformation of *Escherichia coli* by R–Factor DNA," *Proc. Natl. Acad. Sci. USA* 69:2110–2114 (1972).

Cosloy, S.D. and M. Oishi, "Genetic Transformation in *Escherichia coli* K12," *Proc. Natl. Acad. Sci. USA* 70:84–87 (1973).

Cronan, Jr., J.E., "Thermal Regulation of the Membrane Lipid Composition of *Escherichia coli* K12," *J. Biol. Chem.* 250:7074–7077 (1975).

Crowe, J.H. et al., "Stabilization of dry phospholipid bilayers and proteins by sugars," *Biochem. J.* 242:1–10 (1987).

Danilevskaya, O.N. and A.I. Gragerov, "Curing of *Escherichia coli* K12 Plasmids by Coumermycin," *Molec. Gen. Genet.* 178:233–235 (1980).

de Mendoza, D. et al., "Overproduction of cis–Vaccenic Acid and Altered Temperature Control of Fatty Acid Synthesis in a Mutant of *Escherichia coli*," *J. Bacteriol.* 151:1608–1611 (1982).

de Mendoza, D. et al., "Thermal Regulation of Membrane Fluidity in *Escherichia coli*," *J. Biol. Chem.* 258:2098–2101 (1983).

de Mendoza, D. and J.E. Cronan Jr., "Thermal regulation of membrane fluidity in bacteria," *TIBS* 8:49–52 (1983).

Dente, L. et al., "pEMBL: a new family of single stranded plasmids," *Nucleic Acids Research* 11:1645–1655 (1983).

Dityatkin, S.Ya. and B.N. Il'yashenko, "Acceptor properties of freeze–thawed bacteria in relation to isolated plasmid DNA," *Chem. Abs.* 89:295, Abstract No. 176192r (1978).

Dityatkin, S.Ya. and B.N. Ilyashenko, "Frozen and thawed bacteria as recipients of isolated phage and plasmid DNA," *Chem. Abs.* 90:322, Abstract No. 183010d (1979).

Dutyatkin, S.Ya. and B.N. Il'yashenko, "Chromosomal transformation of frozen–thawed bacteria," *Chem. Abs.* 90:286–287, Abstract No. 148301c (1979).

Gombos, Z. et al., "Unsaturation of fatty acids in membrane lipids enhances tolerance of the cyanobacterium Synechocystis PCC6803 to low–temperature photoinhibition," *Proc. Natl. Acad. Sci. USA* 89:9959–9963 (1992).

Green, J.L. and C.A. Angell, "Phase Relations and Vitrification in Saccharide–Water Solutions and the Trehalose Anomaly," *J. Phys. Chem.* 93:2880–2882 (1989).

Hanahan, D., "Techniques for Transformation of E. coli," *DNA cloning. Vol. I, a practical approach* . Glover, D.M., ed., IRL Press Limited, Oxford, England, pp. 109–135 (1985).

Hanahan, D. et al., "Plasmid Transformation of *Escherichia coli* and Other Bacteria," *Meth. Enzym.* 204:63–113 (1991).

Hatley, R.H.M. et al., "The Stabilization of Labile Biochemicals by Undercooling," *Process Biochem.* 22:169–172 (1987).

Hatley, R.H.M. and F. Franks, "Variation in Apparent Enzyme Activity in Two–Enzyme Assay Systems: Phosphoenolpyruvate Carboxylase and Malate Dehydrogenase," *Biotechnol. & Appl. Biochem.* 11:367–370 (1989).

Heckly, R.J. and J. Quay, "A Brief Review of Lyophilization Damage and Repair in Bacterial Preparations," *Cryobiology* 18:592–597 (1981).

Inoue, H. et al., "High efficiency transformation of *Escherichia coli* with plasmids," *Gene* 96:23–28 (1990).

Konev, S. V. et al., "Membrane structural mechanism of the development of competence in *Escherichia coli* cells to calcium–dependent transfection by bacteriophage λ DNA," *Chem. Abs.* 89:295, Abstract No. 176191q (1978).

Lin, J.–J. And J. Kuo, "AFLP™: A Novel PCR–Based Assay for Plant and Bacterial DNA Fingerprinting," Focus 17:66–70 (1995).

*Merck Index: An Encyclopedia of Chemicals, Drugs, and Biologicals*, 11th edition, Budavari, S. et al., eds., Merck & Co., Inc., Rahway, NJ, p. 3 (1989).

Messing, J., "M13mp2 and derivatives: A molecular cloning system for DNA sequencing, strand–specific hybridization, and in vitro mutagenesis," in *Recombinant DNA. Proceedings of the Third Cleveland Symposium on Macromolecules, Cleveland, Ohio, Jun. 22–26, 1981*, Walton, A.G., ed., Elsevier Scientific Publishing Co., Amsterdam, The Netherlands, pp. 143–153 (1981).

Morrison, D.A., "Transformation and Preservation of Competent Bacterial Cells by Freezing," *Meth. Enzym.* 68:326–331 (1979).

Norgard, M.V. et al., "Factors affecting the transformation of *Escherichia coli* strain $_x$1776 by pBR322 plasmid DNA," *Gene* 3:279–292 (1978).

Polisky, B. et al., "Specificity of substrate recognition by the EcoRI restriction endonuclease," *Proc. Natl. Acad. Sci. USA* 72:3310–3314 (1975).

Pope, B. and H.M. Kent, "High efficiency 5 min transformation of *Escherichia coli*," *Nucleic Acids Research* 24:536–537 (Feb. 1996).

Reusch, R.N. et al., "Poly–β–Hydroxybutyrate Membrane Structure and Its Relationship to Genetic Transformability in *Escherichia coli*," *J. Bacteriol.* 168:553–562 (1986).

Sambrook, J. et al., "Plasmid Vectors: Preparation and Tranformation of Competent E. coli," In: *Molecular Cloning: A Laboratory Manual, 2nd Ed.*, Cold Spring Harbor Laboratory Press, Cold Spring Harbor, New York, pp. 1.74–1.84 (1989).

Simione Jr., F.P., "Key Issues Relating to the Genetic Stability and Preservation of Cells and Cell Banks," *J. Parenteral Sci. & Technol.* 46:226–232 (1992).

Suzuki, M. and A.A. Szalay, "Bacterial Transformation Using Temperature–Sensitive Mutants Deficient in Peptidoglycan Synthesis," *Meth. Enzym.* 68:331–342 (1979).

Tang, X. et al., "The optimization of preparations of competent cells for transformation of E. coli," *Nucl. Acids Res.* 22:2857–2858 (1994).

Trinh, T. et al., "STBL2™: An *Escherichia coli* Strain for the Stable Propagation of Retroviral Clones and Direct Repeat Sequences," *FOCUS* 16:78–80 (1994).

Ulrich, A.K. et al., "Genetic and Biochemical Analyses of *Escherichia coli* Mutants Altered in the Temperature–Dependent Regulation of Membrane Lipid Composition," *J. Bacteriol.* 154:221–230 (1983).

van Die, I.M. et al., Transformation in *Escherichia coli*: Studies on the Role of the Heat Shock in Induction of Competence, *J. Gen. Microbio.* 129:663–670 (1983).

Wada, H. et al., "Contribution of membrane lipids to the ability of the photosynthetic machinery to tolerate temperature stress," *Proc. Natl. Acad. Sci. USA* 91:4273–4277 (1994).

Weisburd, S., "Death–Defying Dehydration," *Science News* 133:107–110 (1988).

Life Technologies, Inc. 1993–1994 Catalogue and Reference Guide, GIBCO BRL, Gaithersburg, MD, pub., pp. 6–10 and 9–4 (1993).

\* cited by examiner

US 6,274,369 B1

METHOD CAPABLE OF INCREASING COMPETENCY OF BACTERIAL CELL TRANSFORMATION

CROSS REFERENCE TO RELATED APPLICATIONS

This application is based upon and claims priority from U.S. Provisional Application No: 60/011,040 filed Feb. 2, 1996.

FIELD OF THE INVENTION

The invention relates to improved bacteria, particularly Escherichia coli (E. coli) bacteria capable of high transformation efficiencies, methods for producing improved bacterial strains capable of high transformation efficiencies, and methods for obtaining high transformation efficiencies with bacteria, particularly E. coli bacteria. Specifically, it relates to methods of producing and using bacteria, particularly E. coli bacteria that contain F' episome genetic material and are capable of exhibiting enhanced transformation efficiencies.

BACKGROUND OF THE INVENTION

High efficiency chemically competent E. coli bacteria (bacterial cells that can be transformed with DNA) are used extensively in the generation of cDNA libraries and the cloning of samples containing small amounts of target sequences. The ability to generate representative cDNA libraries, one in which each mRNA species present in the subject cell is represented in the library, relies on many factors. One of the major factors determining the quality of a cDNA library is the number of clones represented in the library. Using competent bacteria having a high transformation efficiency increases the probability of obtaining rare, under-represented clones in plasmid libraries. Also, when cloning samples containing small amounts of target DNA or cloning the DNA products of complex DNA manipulations such as the DNA products of single or multiple blunt ended ligations, the use of high efficiency bacteria is essential.

Early attempts to achieve transformation of E. coli were unsuccessful and it was generally believed that E. coli was refractory to transformation. However, Mandel and Higa (J. Mol. Bio. 53: 159–162 (1970)) found that treatment with $CaCl_2$ allowed E. coli bacteria to take up DNA from bacteriophage λ. In 1972, Cohen et al. showed $CaCl_2$-treated E. coli bacteria were effective recipients for plasmid DNA (Cohen et al., Proc. Natl. Acad. Sci., 69: 2110–2114 (1972)). Since transformation of E. coli is an essential step or cornerstone in many cloning experiments, it is desirable that it be as efficient as possible (Lui and Rashidbaigi, BioTechniques 8: 21–25 (1990)). Several groups of workers have examined the factors affecting the efficiency of transformation.

Hanahan (J. Mol. Biol. 166: 557–580 (1983), herein incorporated by reference) examined factors that affect the efficiency of transformation, and devised a set of conditions for optimal efficiency (expressed as transformants per μg of DNA added) applicable to most E. coli K12 strains. Typically, efficiencies of $10^7$ to $10^9$ transformants/μg can be achieved depending on the strain of E. coli and the method used (Liu & Rashidbaigi, BioTechiniques 8: 21–25 (1990), herein incorporated by reference).

Many methods for bacterial transformation are based on the observations of Mandel and Higa (J. Mol. Bio. 53: 159–162 (1970)). Apparently, Mandel and Higa's treatment induces a transient state of "competence" in the recipient bacteria, during which they are able to take up DNAs derived from a variety of sources. Many variations of this basic technique have since been described, often directed toward optimizing the efficiency of transformation of different bacterial strains by plasmids. Bacteria treated according to the original protocol of Mandel and Higa yield $10^5$–$10^6$ transformed colonies/μg of supercoiled plasmid DNA. This efficiency can be enhanced 100- to 1000-fold by using improved strains of E. coli (Kushner, In: Genetic Engineering: Proceedings of the International Symposium on Genetic Engineering, Elsevier, Amsterdam, pp. 17–23 (1978); Norgard et al., Gene 3:279–292 (1978); Hanahan, J. Mol. Biol. 166: 557–580 (1983)) combinations of divalent cations ((Kushner, In: Genetic Engineering: Proceedings of the International Symposium on Genetic Engineering, Elsevier, Amsterdam, pp. 17–23 (1978)) for longer periods of time (Dagert and Ehrlich, Gene 6: 23–28 (1979)) and treating the bacteria with DMSO (Kushner, In: Genetic Engineering: Proceedings of the International Symposium on Genetic Engineering, Elsevier, Amsterdam, pp. 17–23 (1978)), reducing agents, and hexamminecobalt chloride (Hanahan (J. Mol. Biol. 166: 557–580 (1983).

Incubation of E. coli. in solutions that contain multivalent cations is an important step in the transformation of E. coli. A number of multivalent cations are capable of affecting DNA transformation of E. coli. In addition to calcium cations, manganese, magnesium and barium cations can affect DNA transformation of E. coli and the use of manganese or barium cations rather than calcium cations has lead to higher transformation efficiencies with some strains of E. coli (Taketo, Z. Naturforsch Sect. C 30: 520–522 (1975); Taketo, Z. Naturforsch Sect. C 32: 429–433 (1975); Taketo & Kuno, J. Biochem. 75: 895–904 (1975)). A variety of other compounds affect transformation efficiencies. Organic solvents and sulhydryl reagents can also influence transformation efficiencies (Hanahan (J. Mol. Biol. 166: 557–580 (1983); Kushner, In: Genetic Engineering: Proceedings of the International Symposium on Genetic Engineering, Elsevier, Amsterdam, pp. 17–23 (1978); Jessee, J. A. and Bloom, F. R., U.S. Pat. No. 4,981,797 (1991)).

Incubation of E. coli at temperatures around 0° C., often on ice, in buffers containing multivalent cations is an important step in the production or generation of competent cells of E coli. A rapid heat shock or temperature transition after incubation of the E. coli with target DNA further improves transformation efficiencies (Mandel and Higra, (J. Mol. Bio. 53: 159–162 (1970)). Typically, the solutions containing E. coli and target DNA are transferred from 0° C. to temperatures between 37 and 42° C. for 30 to 120 seconds. The temperature at which E. coli bacteria are grown prior to incubation at 0° C. can also affect transformation efficiency. Growing E. coli bacteria at temperatures between 25 and 30° C. can improve the transformation efficiency of E. coli bacteria compared with E. coli bacteria grown at 37° C. (Jessee, J. A. and Bloom, F. R., U.S. Pat. No. 4,981,797 (1991)). E. coli bacteria that are grown at temperatures between 25 and 30° C., in contrast to 37° C., may require a heat shock at less than 37 to 42° C., or a heat shock of a shorter duration, for optimal results (Jesse and Bloom, U.S. Pat. No. 4,981,797 (1991); Inoue et al. Gene 96:23–28 (1990)).

Transformation efficiency can be affected by the E. coli strain used. The selection of an E. coli strain that is capable of high transformation with the specific competence protocol adopted is an important step in the development of a procedure to produce E. coli bacteria capable of high transformation efficiencies. Different strains can exhibit different transformation efficiencies depending on the competence protocol used. Lui and Rashidbaigi, *BioTechniques* 8: 21–25 (1990), compared the transformation efficiency of five *E. coli* strains, HB101, RR1, DH1, SCS1 and JV30 and showed that the transformation efficiencies of these strains varied according to the methodology adopted.

A number of procedures exist for the preparation of competent bacteria and the introduction of DNA into those bacteria. A very simple, moderately efficient transformation procedure for use with *E. coli* involves re-suspending log-phase bacteria in ice-cold 50 mM calcium chloride at about $10^{10}$ bacteria/ml and keeping them ice-cold for about 30 min. Plasmid DNA (0.1 mg) is then added to a small aliquot (0.2ml) of these now competent bacteria, and the incubation on ice continued for a further 30 min, followed by a heat shock of 2 min at 42° C. The bacteria are then usually transferred to nutrient medium and incubated for some time (30 min to 1 hour) to allow phenotypic properties conferred by the plasmid to be expressed, e.g. antibiotic resistance commonly used as a selectable marker for plasmid-containing cells. Protocols for the production of high efficiency competent bacteria have also been described and many of those protocols are based on the protocols described by Hanahan (*J. Mol. Biol.* 166: 557–580 (1983).

The F episome is a genetic element that may exist as a free genetic element or become integrated into the bacterial genome. The presence of the F episome, whether in a free or integrated form, has important consequences for the host bacterium. F-positive bacteria exhibit surface appendages called pilli, which provide attachment sites that facilitate the infection of certain RNA and single-stranded DNA viruses. Many *E. coli* strains have been constructed to contain an F plasmid in order to facilitate the infection of those strains by single-stranded DNA viruses. *E. coli* strains engineered for this purpose include: JM101 (Messing, In *Recombinant DNA: Proceedings of the Third Cleveland Series on Macromolecules,* Elsevier, Amsterdam p 143–153 (1981)); JM105, JM107, JM109 and JM110 (Yanish-Perron et al., *Gene* 33: 103–119 (1985)); TG1 (Gibson, Ph.D. Thesis, Cambridge University, England (1984)); TG2 (Sambrook et al., In *Molecular Cloning: A Laboratory Manual,* Cold Spring Harbor p. 4.14 (1989)); XL1-Blue (Bullock et al., BioTechniques 5.4:376–378 (1987)); XS127 and XS101 (Levinson et al., *Mol. Appl. Genet.* 2:507–517 (1984)); 71/18 (Dente et al., *Nucleic Acids Res.* 11: 1645–1655 (1983)); KK2186 (Zagursky and Berman, *Gene* 27:183–191 (1984)); and MV1184 (Viera and Messing, *Methods Enzymol.* 153: 3–11 (1987)).

Transformation efficiency was not thought to be enhanced by the addition of F' episome genetic material. (Hanahan (*J. Mol. Biol.* 166: 557–580 (1983); Bullock et al. (1987)). Indeed, the addition of a F' episome to the *E. coli* strain AG1 produced an *E. coli* strain (XL1-Blue) with a reduced transformation efficiency (Bullock et al. (1987)). Contrary to this background, Applicants' invention involves the use of F' genetic material to provide modified *E. coli* having improved transformation efficiency compared with *E. coli* without F' genetic material.

Another rapid and simple method for introducing genetic material into bacteria is electoporation (Potter, *Anal. Biochem.* 174: 361–73 (1988)). This technique is based upon the original observation by Zimmerman et al., *J. Membr. Biol.* 67: 165–82 (1983), that high-voltage electric pulses can induce cell plasma membranes to fuse. Subsequently, it was found that when subjected to electric shock (typically a brief exposure to a voltage gradient of 4000–16000 V/cm), the bacteria take up exogenous DNA from the suspending solution, apparently through holes momentarily created in the plasma membrane. A proportion of these bacteria become stably transformed and can be selected if a suitable marker gene is carried on the transforming DNA transformed (Newman et al., *Mol. Gen. Genetics* 197: 195–204 (1982)). With *E. coli,* electroporation has been found to give plasmid transformation efficiencies of $10^9$–$10^{10}$ /μg DNA (Dower et al., *Nucleic Acids Res.* 16: 6127–6145 (1988)).

Bacterial cells are also susceptible to transformation by liposomes (Old and Primrose, In *Principles of Gene Manipulation: An Introduction to Gene Manipulation,* Blackwell Science (1995)). A simple transformation system has been developed which makes use of liposomes prepared from cationic lipid (Old and Primrose, (1995)). Small unilamellar (single bilayer) vesicles are produced. DNA in solution spontaneously and efficiently complexes with these liposomes (in contrast to previously employed liposome encapsidation procedures involving non-ionic lipids). The positively-charged liposomes not only complex with DNA, but also bind to bacteria and are efficient in transforming them, probably by fusion with the cells. The use of liposomes as a transformation or transfection system is called lipofection.

SUMMARY OF THE INVENTION

The present invention provides novel bacterium, particularly novel *E. coli* bacterium, capable of high efficiency transformation, whose efficiency of transformation is enhanced by the introduction of F' episome genetic material. The invention also concerns methods for the use of novel bacteria, particularly novel *E. coli* bacteria, whose efficiency of transformation is enhanced by the introduction of F' episome genetic material. Furthermore, the invention also provides methods for constructing bacteria capable of high efficiency transformation, whose efficiency of transformation is enhanced by the introduction of F' episome genetic material. Indeed, the invention may be used for the insertion of exogenous DNA sequences from other E. coli bacteria or other organisms into the novel bacteria of the present invention.

DETAILED DESCRIPTION

One object of the present invention is to provide a bacterium containing F' genetic material capable of an enhanced transformation efficiency. A particular object of the present invention is to provide an *E. coli* bacterium containing F' genetic material capable of an enhanced transformation efficiency.

A further object of the present invention is to provide a process for producing an Enterobacteriacea (especially an *E. coli* bacterium) containing F' genetic material capable of an enhanced transformation efficiency, comprising the following steps: (a) introducing F' genetic material into a bacterium; (b) selecting the bacterium containing F' genetic material; and (c) recovering the bacterium containing F' genetic material.

Another object of the present invention is to provide a process for preparing competent bacteria comprising the following steps: (a) growing a bacterium (especially an *E. coli* bacterium) containing F' genetic material capable of an enhanced transformation efficiency in a growth-conductive medium; and (b) rendering the bacterium competent.

The present invention further concerns a novel bacterium, especially an Enterobacteriacea, and particularly a novel *E. coli* bacterium capable of high efficiency transformation, whose efficiency of transformation is enhanced by the introduction of F' episome genetic material. The present invention also concerns processes for transforming *E. coli* bacterium containing F' genetic material that are capable of enhanced transformation efficiencies.

The present invention pertains to bacteria capable of high efficiency transformation. Such bacteria may be any bacteria whose efficiency of transformation can be enhanced by the introduction of F' episome genetic material. Examples of suitable bacteria include bacteria of the Enterobacteriacea, and in particular, bacteria of the genera Escherichia, Salmonella, especially *E. coli* and Salmonella species. In a preferred embodiment, the bacterium of the present invention may be any *E. coli* strain capable of high efficiency transformation whose efficiency of transformation is enhanced by the introduction of F' episome genetic material. In a further preferred embodiment of the present invention, the bacterium may be any *E. coli* K strain or derivative or equivalent thereof. As used herein, a "derivative" of a bacterium is any bacterium that results from any alteration (or series or alterations), naturally occurring or otherwise, of that bacterium. As used herein, an "equivalent" of a bacterium is any bacterium that has a transformation efficiency (as measured by transformants/$\mu$g DNA added) that is equivalent to the transformation efficiency of that bacterium. In an even more preferred embodiment, the bacterium of the present invention will preferably be a derivative of *E. coli* K, such as MM294 (Meselson & Yuan, *Nature* 217:1110–1114 (1968), or a derivative or equivalent thereof. In a further even more preferred embodiment, the bacterium of the present invention will be preferably be *E. coli* DH5α or a derivative or equivalent thereof, whose efficiency of transformation is enhanced by the introduction of F' episome genetic material. In the most preferred embodiment, the bacterium of the present invention will be more preferably be *E. coli* DH5α, whose efficiency of transformation is enhanced by the introduction of F' episome genetic material.

Transformation, in the context of the current invention, is the process by which exogenous DNA is inserted into a bacterium, causing the bacterium to change its genotype and/or phenotype. Such a change in genotype or phenotype may be transient or otherwise. Exogenous DNA is any DNA, whether naturally occurring or otherwise, from any source that is capable of being inserted into any organism. Preferably, exogenous DNA is any DNA, whether naturally occurring or otherwise, from any source that is capable of being inserted into bacteria. More preferably, exogenous DNA is any DNA, whether naturally occurring or otherwise, from any source that is capable of being inserted into DH5α. Even more preferably, exogenous DNA is any DNA, whether naturally occurring or otherwise, from any source that is capable of being inserted into DH5α bacteria capable of high efficiency transformation, whose efficiency of transformation is enhanced by the introduction of F' episome genetic material. Such exogenous DNA includes, without limitation, plasmid DNA and lambda DNA.

The bacteria of the present invention are capable of acting as a recipient for inserted exogenous DNA. In a preferred embodiment, bacteria capable of acting as a recipient for exogenous DNA are prepared by inoculating medium which supports their growth. In a more preferred embodiment, *E. coli* DH5α bacteria containing F' genetic material capable of an enhanced transformation efficiency are grown at 28° C. in SOB media (20 g bacto-trytone, 5 g bacto-yeast extract, 5 g NaCl, per liter, 2.5 mM KCl, 10 mm MgCl$_2$ equilibrated to pH 7.0 with NaOH) media containing additional multivalent cations until the optical density of the solution was 0.3 O.D.$_{550}$ In an even more preferred embodiment, *E. coli* DH5α bacteria containing F' genetic material capable of an enhanced transformation efficiency are grown at 28° C. in SOB media containing 20 mM magnesium cations until the optical density of the solution is 0.3 O.D.$_{550}$ In a preferred embodiment, the bacteria are harvested by centrifugation and resuspended in a solution capable of inducing competence in *E. coli*. In a more preferred embodiment, *E. coli* DH5α bacteria containing F' genetic material capable of an enhanced transformation efficiency are harvested by centrifugation at 4° C. for 10 minuets at 4,000 rpm and resuspended in FSB (10 mM potassium acetate, 100 mM potassium chloride, 45 mM maganese (II) chloride tetrahydrate, 10 mM calcium chloride dihydrate, 3 mM hexammecolbalt (III) chloride, 10% (volume:volume) glycerol, 5% (weight:volume) sucrose, pH 6.4). In an even more preferred embodiment, the re-suspended bacteria containing F' genetic material capable of an enhanced transformation efficiency are subsequently treated with DMSO and can be stored at 70° C. for up to 1 year.

In a preferred embodiment, the bacteria are thawed on ice, mixed with exogenous DNA, incubated on ice, and heat treated. In a more preferred embodiment, the frozen *E. coli* DH5α bacteria containing F' genetic material are thawed on ice for 10 to 15 minuets, mixed with exogenous DNA, incubated on ice for 30 minutes, and heat treated at 42° C. for 45 seconds.

In another embodiment of the present invention, the bacteria are treated with high voltage electric pulses in a solution containing exogenous DNA. In a more preferred alternative embodiment of the present invention, the bacteria are *E. coli* DH5α containing F' genetic material, and are mixed with exogenous DNA and then treated with a brief voltage gradient of 4,000 to 16,000 V/cm.

In a preferred embodiment, high efficiency transformation is preferably $10^8$ or greater transformed bacteria per $\mu$g of purified plasmid DNA. High efficiency transformation is more preferably $10^9$ or greater transformed bacteria per $\mu$g of purified plasmid DNA.

The present invention also concerns novel *E. coli* bacteria capable of high efficiency transformation, whose efficiency of transformation is enhanced by the introduction of F' episome genetic material. As used herein, such efficiency is said to be "enhanced" if the presence of F' episome genetic material increases the efficiency of transformation of a bacterium. In the preferred embodiment the efficiency of the present invention is enhanced by a factor of greater than one. In a more preferred embodiment, the transformation efficiency of the present invention is enhanced by 2–4 fold. In a even more preferred embodiment, the transformation efficiency of the present invention is enhanced by greater than 4 fold.

The present invention concerns a novel *E. coli* bacterium capable of high efficiency transformation, where said transformation alters the bacterium's genotype and/or transiently alters the bacterium's phenotype. The genotype of an organism is the genetic constitution of an organism. The phenotype of the organism are the characteristics of an organism.

The present invention concerns novel *E. coli* bacteria capable of high efficiency transformation, whose efficiency of transformation is enhanced by the introduction of certain F' episome genetic material. In a preferred embodiment, the bacteria contains all or part of the F' episome genetic material integrated into the *E. coli* chromosome. In another preferred embodiment, the bacteria contains all or part of the F' episome genetic material on a self replicating DNA molecule. In a more preferred embodiment, all or part of the F' episome genetic material is genetically linked to a selectable marker. In an even more preferred embodiment, the F' episome genetic material is linked to an selectable marker providing resistance to an antibiotic, such as a gene providing resistance to tetracycline. In the most preferred embodiment, the F' episome genetic material is derived from the F' episome of XL1-Blue.

The present invention also concerns processes for constructing E. coli bacteria containing F' genetic material capable of enhanced transformation efficiencies. In a preferred embodiment, the bacteria of the current invention is obtained by introducing F' genetic material into an E. coli bacterium. In a more preferred embodiment of the present invention, the bacterium of the present invention is obtained by mating E. coli XL1-Blue and E. coli DH5α bacteria. In an even more preferred embodiment of the present invention, the bacteria of the present invention is obtained by mating E. coli XL1-Blue and E. coli DH5α pCM301Δ bacteria (Tucker et al. Cell 36:191–201(1984)).

Having now generally described the invention, the same will be more readily understood through reference to the following examples which are provided by way of illustration, and are not intended to be limiting of the present invention unless specified.

EXAMPLE 1

Construction of the DH5α F'1B Strain

XL1-Blue and XL2-Blue E. coli strains can be obtained from Stratagene (11011 N. Torrey Pines Road, La Jolla, Calif. 92037). DH5α E. coli strains can be obtained from Life Technologies, Inc., P.O. Box 68, Grand Island, N.Y. 14072-0068. To distinguish between the genotypes of DH5α, XL1-Blue and XL2-Blue E. coli strains, DH5α is transformed with a temperature-sensitive plasmid pCM301Δ that exhibits ampicillin resistance. E. coli strains DH5α/pCM301Δ, XL1-Blue and XL2-Blue are then streaked out on LB agar plates (LB agar plates: 15 grams per liter bacto-agar in Lennox LB Broth (10 grams tryptone, 5 grams yeast extract, 5 grams NaCl per liter)) containing appropriate antibiotics. The XL1-Blue and XL2-Blue strains are streaked out on LB plates that contained 15 μg/ml tetracycline whereas the DH5α/pCM301Δ bacteria are streaked out on LB plates containing 100 μg/ml ampicillin. The plates are incubated overnight at 30° C.

Individual colonies from each strain are isolated and placed into 1 ml of LB medium and grown at 30° C., without shaking, for 4 hours. After the 4 hours, two matings of the E. coli strains are set up by mixing 0.5 ml of the DH5α/pCM301Δ culture with 0.1 ml of the XL1-Blue or XL2-Blue culture and 0.5 ml of fresh Lennox LB Broth medium in a 15 ml culture tube that is incubated for 30 minutes at 30° C. Post-mating, the bacteria are diluted either $10^{-2}$ or $10^{-4}$ with Lennox LB Broth and 100 μl of the resultant solution is applied to LB plates containing 100 μg/ml ampicillin and 15 μg/ml tetracycline. These plates are incubated for between 16 to 18 hours at 30° C. Ten individual colonies are selected from the plates and restreaked for single colony isolation on LB AMP$_{100}$ TET$_{15}$ plates (LB agar plates containing 100 μg/ml ampicillin and 15 μg/ml tetracycline), which are then incubated overnight at 30° C. The colonies are purified through two additional rounds of restreaking on LB AMP$_{100}$ TET$_{15}$ plates grown at 30° C. overnight. The resulting colonies can be designated DH5α F'1 and F'2 corresponding to products from the DH5α/pCM301Δ/XL1-Blue mating and the DH5α/pCM301Δ/XL2-Blue respectively. The temperature sensitive pCM301Δ plasmids are eliminated (cured) from the DH5α F'1 and DH5α F'2 isolates by growing them at 42° C. in a shaking incubator (250 rpm) for 16 to 18 hours in 1.5 ml of LB containing 15 μg/ml tetracycline. The cured bacteria are purified by streaking for single colonies on LB TET$_{15}$ plates and incubated at 37° C. for 16 to 18 hours. Individual clones are further purified by restreaking on LB TET$_{15}$ plates and incubated for an additional 16 to 18 hours at 37° C. The genotype of the DH5α F'1 and DH5α F'2 isolates are confirmed by attempting to grow the isolates on LB AMP$_{100}$ plates and by growing the isolates on LB X-gali IPTG plates (LB agar plates containing 100 μg/ml X-gal and 40 μg/ml IPTG).

EXAMPLE 2

Production of Competent Bacteria

Working seeds of the DH5α F'1, DH5α F'2, XL1-Blue, XL2-Blue and DH5α strains are generated from single colonies cycled at 28° C. for three days. Cycling single colonies involves isolating a single colony for each restreaked strain and restreaking the isolating colony on the appropriate media. The colonies are then grown for 16–18 hours at 28° C. From these plates a single isolated colony from each strain is selected and then restreaked on the appropriate media and grown for 16–18 hours at 28° C. The process of growing the colonies for 16–18 hours at 28° C. is repeated three times to acclimate the strain to the growth temperature.

Individual colonies are diluted in 1.5 ml of SOB media. 900 μgl of the diluted colonies are used to inoculate 50 ml of SOB media with 15 μg/ml tetracycline contained in a 500 ml side baffled flask. The bacteria are then grown at 28° C. in a shaking incubator (250 rpm) until the optical density of the solutions is between 0.5 to 0.7 OD$_{550}$ (about 8 to 10 hours). Seeds are produced by mixing a 10 ml sample from the culture with 10 ml of SOB:glycerol (60:40) in a 50 ml tube. The mixture is then incubated on ice for 10 minutes. Aliquots (0.5 ml) of the seeds are distributed into 1.2 ml Nunc cryotubes and frozen for 5 minutes in a dry ice:ethanol bath. Seeds are stored at −70° C. and used for up to 1 year.

Competent bacteria are produced using a modification of the procedure developed by Hanahan (J. Mol. Biol. 166: 557–580 (1983). A seed culture of each strain (DH5α F', XL1-Blue, XL2-Blue and DH5 α) are thawed at room temperature and diluted in a ratio of 1:100 with 1 ml SOB containing 20 mM Mg$^{++}$. Aliquots (0.25 ml) of the diluted seed are used to inoculate 2.8 liter baffled Fernbach flasks that contained 1.7 L of SOB/20 mM Mg$^{++}$/100 μg/ml tetracycline. The cultures are incubated at 28° C. in a shaking incubator (275 rpm), until they reach an OD$_{550}$ of 0.5. The bacteria are then harvested by centrifugation in 250 ml Corning centrifuge tubes at 4000 rpm for 10 minutes at 4° C. (2300g). The supernatant is then drained from the tubes and the bacteria are resuspended in 20 ml FSB+5% sucrose (10 mM potassium acetate, 100 mM potassium chloride, 45 mM maganese (II) chloride tetrahydrate, 10 mM calcium chloride dihydrate, 3 mM hexammecolbalt (III) chloride, 10% (volume:volume) glycerol, 5% (weight:volume) sucrose, pH 6.4). The resuspended bacteria are incubated on ice for 15 minutes. Competence is enhanced by two sequential additions of 0.7 ml DMSO with a 10 minute incubation on ice between additions. After the DMSO additions, the competent bacteria are further incubated on ice for 5 minutes. The competent bacteria are then frozen for 5 minutes in 1.2 ml Nunc Cryotubes containing 0.25 ml of bacteria in a dry ice:ethanol bath. Frozen competent bacteria are stored at −70° C. and are stable for up to 1 year.

EXAMPLE 3

Transformation Procedures

Competent bacteria are removed from −70° C. freezer and thawed on wet ice for about 10 to 15 minutes. Immediately after thawing, the bacteria are gently transferred into pre-chilled polypropylene tubes and gently agitated. Transformation efficiencies, of the competent bacteria are determined by mixing 5 μl (0.05 ng) of control pUC19 DNA to each tube of competent bacteria and incubating the bacteria on ice for 30 minutes. A heat-shock of the bacteria is carried out at 42° C. for 45 seconds in water bath. Care is taken not to shake the bacteria during the period of the time the bacteria are undergoing heat treatment. The transformation mixtures are then placed on ice for 2 minutes prior to the addition of 0.9 ml of room temperature SOC (SOC medium is identical to SOB medium except that it contains 20 mM glucose) to the transformation mix. The transformation mixtures are incubated at 37° C. for 1 hour in a shaker (225 rpm). The transformation reactions are then diluted in a ratio of 1:100 with SOC medium and 50 μl or 100 μl of the diluted samples are spread on LB plates with 100 μg/ml ampicillin. The plates are then incubated overnight at 37° C.

The total transformants per reaction are determined by adding 25 ng of control pUC19 DNA to each 17×100 mm polypropylene tube of competent bacteria. The DNA are added by moving the pipette through the bacteria and gently taping the bottom of the tube. The bacteria are incubated on ice for 30 minutes and heat-shocked at 42° C. for 45 seconds in water bath. Care is taken not to shake the bacteria during the period of the time the bacteria are undergoing heat treatment. The transformation mix is placed on ice for 2 minutes. After two minutes, 0.9 ml of room temperature SOC is added to the transformation mixture and incubated at 37° C. for 1 hour in a shaker (225 rpm). The transformation reactions are diluted in a ratio of 1:10,000 with SOC medium and then 100 μl of this dilution is spread on LB or YT plates that contained 100 μg /ml ampicillin. The plates are incubated overnight at 37° C.

A viable cell count of the sample is determined by diluting the bacteria in SOC to $10^{-7}$ and then spreading 100 μl from each dilution on LB plates. These plates are incubated overnight at 37° C.

| Sample | Transformation Efficiency (transformants/μg) | Viable Bacteria | Total Transformants |
| --- | --- | --- | --- |
| MAX EFFICIENCY | | | |
| DH5α | $1.1 \times 10^9$ | $1.3 \times 10^9$ | $7.7 \times 10^6$ |
| DH5α | $1.4 \times 10^9$ | $1.4 \times 10^9$ | $4.5 \times 10^6$ |
| DH5α F1 | $6.9 \times 10^9$ | $2.5 \times 10^9$ | $17 \times 10^6$ |
| DH5α F2 | $6.9 \times 10^9$ | $3.1 \times 10^9$ | $21 \times 10^6$ |
| XL1-Blue | $3.2 \times 10^9$ | $2.4 \times 10^9$ | $11 \times 10^6$ |
| XL2-Blue | $4.3 \times 10^9$ | $2.1 \times 10^9$ | $15 \times 10^6$ |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A kit for transforming DNA into competent bacteria, said kit comprising one or more vials, each of said vials containing an aliquot of a preparation of competent bacteria, said preparation comprising isolated bacteria derived from *Escherichia coli* DH5α and additionally comprising F' genetic material derived from *Escherichia coli* XL1, wherein said isolated bacteria exhibit a higher transformation efficiency than said *Escherichia coli* DH5α which does not contain said F' genetic material derived from *Escherichia coli* XL1.

2. A kit for transforming DNA into competent bacteria, said kit comprising one or more vials, each of said vials containing an aliquot of a preparation of competent bacteria, said preparation comprising isolated bacteria derived from *Escherichia coli* DH5α and additionally comprising F' genetic material derived from *Escherichia coli* XL2, wherein said isolated bacteria exhibit a higher transformation efficiency than said *Escherichia coli* DH5α which does not contain said F' genetic material derived from *Escherichia coli* XL2.

3. A process for producing an *E. coli* bacterium capable of an enhanced transformation efficiency, said process comprising (a) introducing F' genetic material into an *E. coli* bacterium that does not contain F' genetic material; and (b) recovering an *E. Coli* bacterium containing said F' genetic material, wherein after said *E. coli* bacterium containing said F' genetic material is rendered competent, said *E. coli* bacterium containing said F' genetic material exhibits a higher transformation efficiency than said *E. coli* bacterium that does not contain F' genetic material.

4. The process according to claim 3, wherein said bacterium is DH5α.

5. The process according to claim 3, wherein said F' genetic material is derived from *Escherichia coli* XL2.

6. The process according to claim 3, wherein said F' genetic material is derived from *Escherichia coli* XL1.

7. A process for preparing competent bacteria, said process comprising (a) introducing F' genetic material into an *E. coli* bacterium that does not contain F' genetic material;

(b) recovering an *E. coli* bacterium containing said F' genetic material, and (c) rendering said *E. coli* bacterium containing said F' genetic material competent, wherein after said *E. coli* bacterium containing said F' genetic material is rendered competent, said *E. coli* bacterium containing said F' genetic material exhibits a higher transformation efficiency than said *E. coli* bacterium that does not contain F' genetic material.

8. The process according to claim 7, wherein said bacterium is DH5α.

9. The process according to claim 7, wherein said F' genetic material is derived from *Escherichia coli* XL1.

10. The process according to claim 7, wherein said F' genetic material is derived from *Escherichia coli* XL2.

11. A preparation of competent *E. coli* bacteria obtained by the process of claim 7.

12. The preparation according to claim 11, wherein said bacterium is DH5α.

13. The preparation according to claim 11, wherein said F' genetic material is derived from *Escherichia coli* XL1.

14. The preparation according to claim 11, wherein said F' genetic material is derived from *Escherichia coli* XL2.

* * * * *